(12) United States Patent
Shukla et al.

(10) Patent No.: US 6,416,716 B1
(45) Date of Patent: Jul. 9, 2002

(54) SAMPLE PREPARATION DEVICE WITH EMBEDDED SEPARATION MEDIA

(76) Inventors: Ashok Kumar Shukla; Mukta Shukla; Amita Shukla, all of 10423 Popkins Ct., Woodstock, MD (US) 21163

( * ) Notice: Subject to any disclaimer, the term of this patent is extended or adjusted under 35 U.S.C. 154(b) by 0 days.

(21) Appl. No.: 09/839,931

(22) Filed: Apr. 20, 2001

(51) Int. Cl.[7] .................... B01L 11/00; G01N 1/00; C12Q 1/42; B01D 15/08

(52) U.S. Cl. .................. 422/101; 210/656; 210/500; 210/198.2; 435/21; 436/174

(58) Field of Search ................ 436/74; 494/1; 210/500, 656, 198.2; 435/21

(56) References Cited

U.S. PATENT DOCUMENTS

| | | | | |
|---|---|---|---|---|
| 3,513,092 A | * | 5/1970 | Matherine, Jr. | 210/198.3 |
| 4,793,920 A | * | 12/1988 | Cortes et al. | 210/198.2 |
| 5,453,163 A | * | 9/1995 | Yan | 204/180.1 |
| 5,660,797 A | * | 8/1997 | Jarvimaki | 422/100 |
| 5,719,322 A | * | 2/1998 | Lansbarkis et al. | 210/198.2 |
| 5,783,308 A | * | 7/1998 | Leendersen | 428/422 |
| 5,939,614 A | * | 8/1999 | Walters et al. | |
| 5,997,746 A | * | 12/1999 | Valaskovic | 210/656 |
| 6,190,559 B1 | * | 2/2001 | Valaskovic | 210/656 |
| 6,200,474 B1 | * | 3/2001 | Kopaciewicz et al. | 210/321.6 |
| 6,301,952 B1 | * | 10/2001 | De Zeeuw et al. | 73/23.35 |

FOREIGN PATENT DOCUMENTS

| | | | | |
|---|---|---|---|---|
| FR | 2498331 A | * | 7/1982 | G01N/31/22 |
| WO | WO 0107162 A1 | * | 2/2001 | |

OTHER PUBLICATIONS

Aldrich Catalog (1994) p. T132, 1008–1009, Gas Chromatography Capillary columns.*
Harris, Daniel, Quantitative Chemical Analysis, 4th Ed. W.H. Freeman and Company, NY (1995) Chapter 23–1, pp. 656–670.*

* cited by examiner

Primary Examiner—Jill Warden
Assistant Examiner—Jennine Brown

(57) ABSTRACT

The present invention relates to a novel device for small sample preparation using tubes and columns, such as capillaries or pipette tips, in which particles of a separation medium, such as particles of a chromatography material used for sample preparation, are directly embedded in the solid material composing the tubes or columns. Most small sample preparation methods currently available cannot prevent sample loss and they are not well suited for small sample volumes. The present invention minimizes sample loss and is well suited for samples with volumes in nanoliters. In the invention described herein, the desired sample, such as a sample composed of biomolecules, is brought in contact with particles of the separation medium embedded on the surface of the device comprised of tubes and columns, according to the present invention. The sample is separated, analyzed, purified or prepared for further analysis as the sample components come in contact with the separation medium embedded in the tubes or columns, according to the present invention. The tubes or columns described in the present invention can be capillaries, pipette tips, combinations thereof, or any other devices suited for the preparation and analysis of small samples with volumes from nanoliters to hundreds of milliliters. The present invention also describes a method for making tubes or columns that have particles of separation media embedded on their surface for sample preparation applications.

16 Claims, 13 Drawing Sheets

SAMPLE PREPARATION DEVICE WITH EMBEDDED SEPARATION MEDIA

FIELD OF THE INVENTION

The present invention relates to a novel device for small sample preparation using tubes and columns, such as capillaries or pipette tips, in which particles of a separation medium, such as particles of a chromatography material used for sample preparation, are directly embedded in the solid material composing the tubes or columns. Most small sample preparation methods currently available cannot prevent sample loss and they are not well suited for small sample volumes. The present invention minimizes sample loss and is well suited for samples with volumes in nanoliters.

In the invention described herein, the desired sample, such as a sample composed of biomolecules, is brought in contact with particles of the separation medium embedded on the surface of the device comprised of tubes and columns, according to the present invention. The sample is separated, analyzed, purified or prepared for further analysis as the sample components come in contact with the separation medium embedded in the tubes or columns, according to the present invention. The tubes or columns described in the present invention can be capillaries, pipette tips, combinations thereof, or any other devices suited for the preparation and analysis of small samples with volumes from nanoliters to hundreds of milliliters. The present invention also describes a method for making tubes or columns that have particles of separation media embedded on their surface for sample preparation applications.

BACKGROUND OF THE INVENTION

A number of methods for separating, purifying or preparing small biological samples currently exist. Yet, many of the available methods present significant disadvantages, which can be overcome by the current invention. Currently, sample preparation is performed using spin columns, filter and separation medium filled chromatography columns and even pipette tips filled or coated with separation media such as chromatography materials. Sample preparation using these available devices is performed through centrifugation, gravitation, vacuum suction, and pressure application or by syringe-based or pressure-based sample delivery through the columns or tips. Such columns are used for the separation and purification of small sample volumes from nanoliters to milliliters. The samples purified using these methods can be any type of samples such as samples containing biomolecules such as proteins, DNA, nucleic acids and other biological molecules. Many different types of separation media are used in currently available columns including but not limited to chromatography materials such as gel-filtration, affinity, ion-exchange, reverse-phase, and silica or modified-silica materials.

Although many different analytical methods for small sample separation and purification have been developed, a number of problems, such as the slow speed of the separation process and the loss of sample volume limit the quality of results obtained using these methods. For example, in spin columns and small sample chromatography columns, filters are used to hold the separation medium within the column such that separate filters are placed above and/or below the separation medium in the column. In such columns the sample flows through the filters, in addition to the separation media, before being collected or retrieved for further analysis. One of the main problems with filters is that they slow the rate at which the sample passes through the column and they result in the loss of sample on the filter material.

At present, most macro spin columns and micro spin columns contain a filter at their bottom end. The sample loss is especially significant when very small sample volumes are separated using currently available methods. In fact, currently available methods are not well suited for the separation of very small sample volumes in the nanoliters range. Since the concentration of biomolecules in micro volume samples is so small, the retention of molecules on the filter can result in significant loss of the total sample volume. Also, since the volume of the filter is often as large as the volume of the micro volume sample itself, the separation or chromatography process is adversely affected due to the large volume of filter material through which the sample must pass during the separation process.

The filter material may also absorb proteins or biomolecules from the sample, resulting in lower than desirable sample recovery. Also, the filter material may behave differently in different elution media, subsequently interfering with both the quality of the separation process and the volume of the sample retained.

There are some filter-free columns that are currently available for sample preparation. In the most commonly available versions, such columns rely on a solid support matrix in which the separation medium is embedded. The combination of the solid matrix and the separation material is then adhered to a column or pipette tip to create a plug or coating through which the sample passes for sample preparation. In currently available technologies where a plug of the solid matrix and separation material is used, sample flow through the plug is slow, limiting the rate at which samples can be prepared. Also, sample loss in the plug limits the use of such technology for the preparation of very small samples.

SUMMARY OF THE INVENTION

In the present invention we describe a sample preparation device consisting of one or more tubes or columns where at least one of said tubes or columns contains particles of a separation medium directly embedded in the material comprising said tube or column. Said tubes or columns may be closed or open at one or both ends to impede or permit the flow of the sample through the tube or column. Said tubes or columns can be composed of any polymer materials. Thus, the sample preparation device described in the present invention is free of any filters or solid matrices that can potentially slow the rate of sample preparation and result in sample loss. Furthermore, the sample preparation device described in the present invention can be created such that it is suited for the separation and preparation of very small sample volumes, in the nanoliter range. The separation medium used in the present invention can consist of one or more types of different separation media such as chromatography materials such as gel-filtration, ion-exchange, reverse-phase, and silica or modified silica media.

Once desired components of a sample, such as biomolecules, bind to the separation media embedded in the tubes or columns, the sample components can then be eluted from the separation media using different solvents. The device described in the present invention is also very well suited for automated processes such as high throughput screening.

The various features of novelty, which characterize the invention, are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

The foregoing and still other objects of this invention will become apparent, along with various advantages and features of novelty residing in the present embodiments, from study of the following drawings, in which.

DESCRIPTION OF THE PREFERRED EMBODIMENTS

Figure 1:
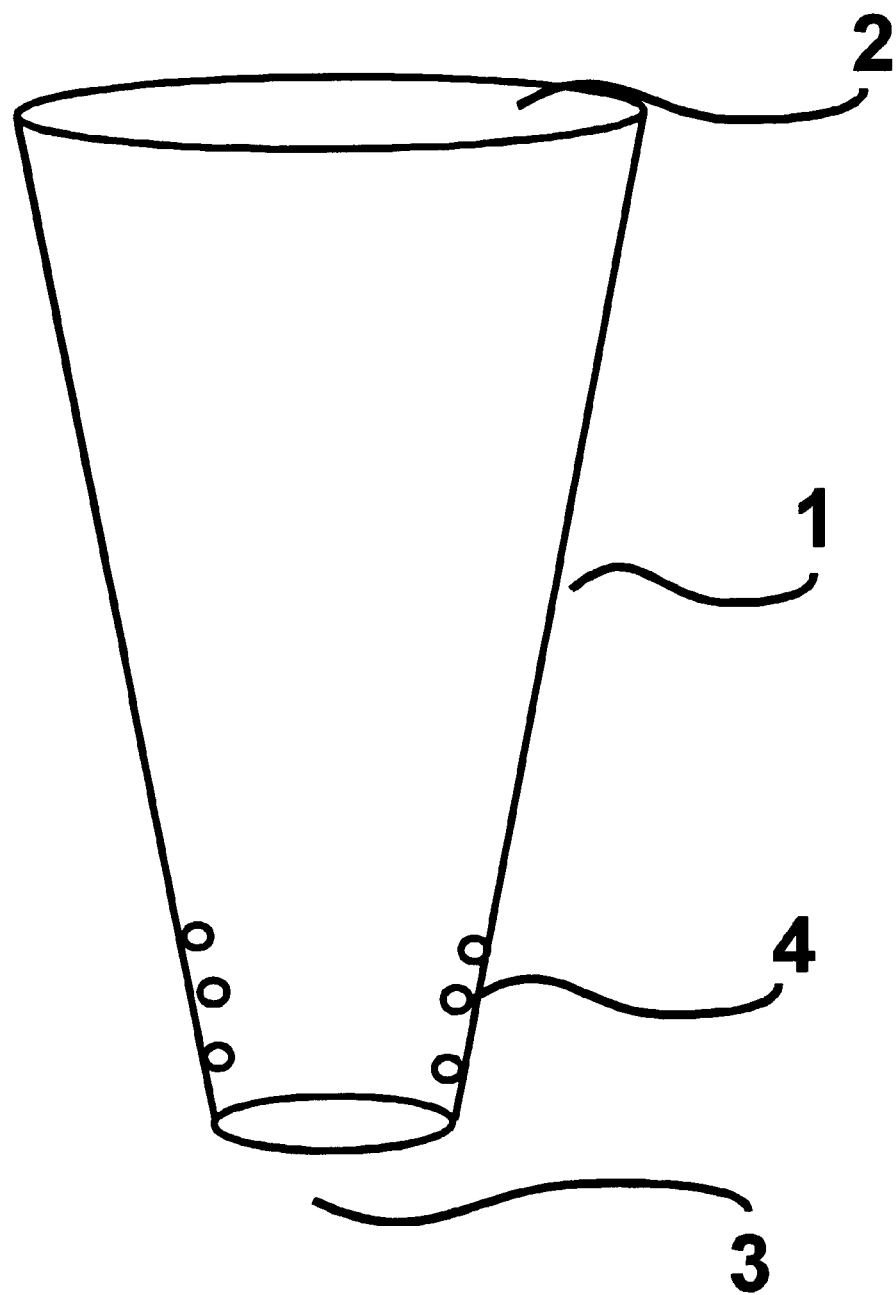
FIG. 1 is an expanded view of one embodiment of a tube, according to the present invention, wherein said tube has a top open end and a bottom open end and wherein particles of a separation medium are directly embedded on the interior surface of said tube.

Referring to the drawings, FIG. 1 shows a tube or column, according to the present invention. The tube (1), as shown in this figure, has an open top end (2) and an open bottom end (3).

Also, particles of a separation medium (4) are shown to be embedded on the inner surface of the tube (1) such that said particles (4) adhere to the sides of the tube (1). A sample can be passed through the tube such that said sample enters the tube (1) at the top end (2) and exits at the bottom end (3); enters the tube (1) at the top end (2) and exits at the top end (2); or, enters the tube (1) at the bottom end (3) and exits the tube at the bottom end (3).

Figure 2:
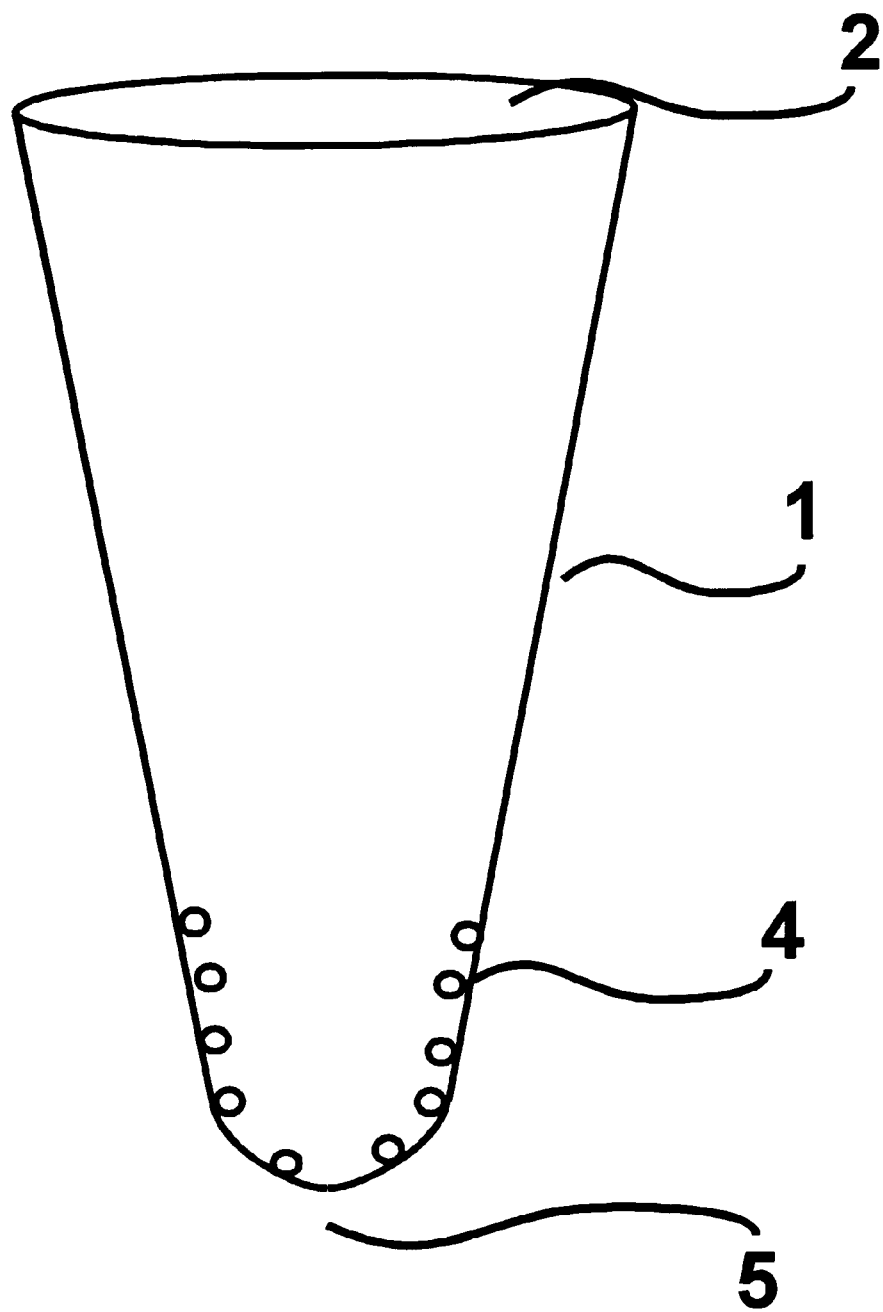
FIG. 2 is an expanded view of one embodiment of a tube, according to the present invention, wherein said tube has a top open end and a bottom closed end and wherein particles of a separation medium are directly embedded on the interior surface of said tube.

Alternatively, as shown in FIG. 2, said tube or column can be in a configuration where said tube (1) has an open top end (2) and a closed bottom end (5). Also, as shown in this figure, particles of a separation medium (4) are embedded on the interior surface of said tube (1). While two possibilities for the configuration of the bottom end (3 and 5) are shown, it is understood that each end of the tube (1) can be open or closed.

Therefore, the ends of said tube (1) are selected from the group comprised of an open top end and an open bottom end; an open top end and a closed bottom end; a closed top end and an open bottom end; a closed top end and a closed bottom end; a tapered open end; a tapered closed end; and, combinations thereof.

Figure 3:
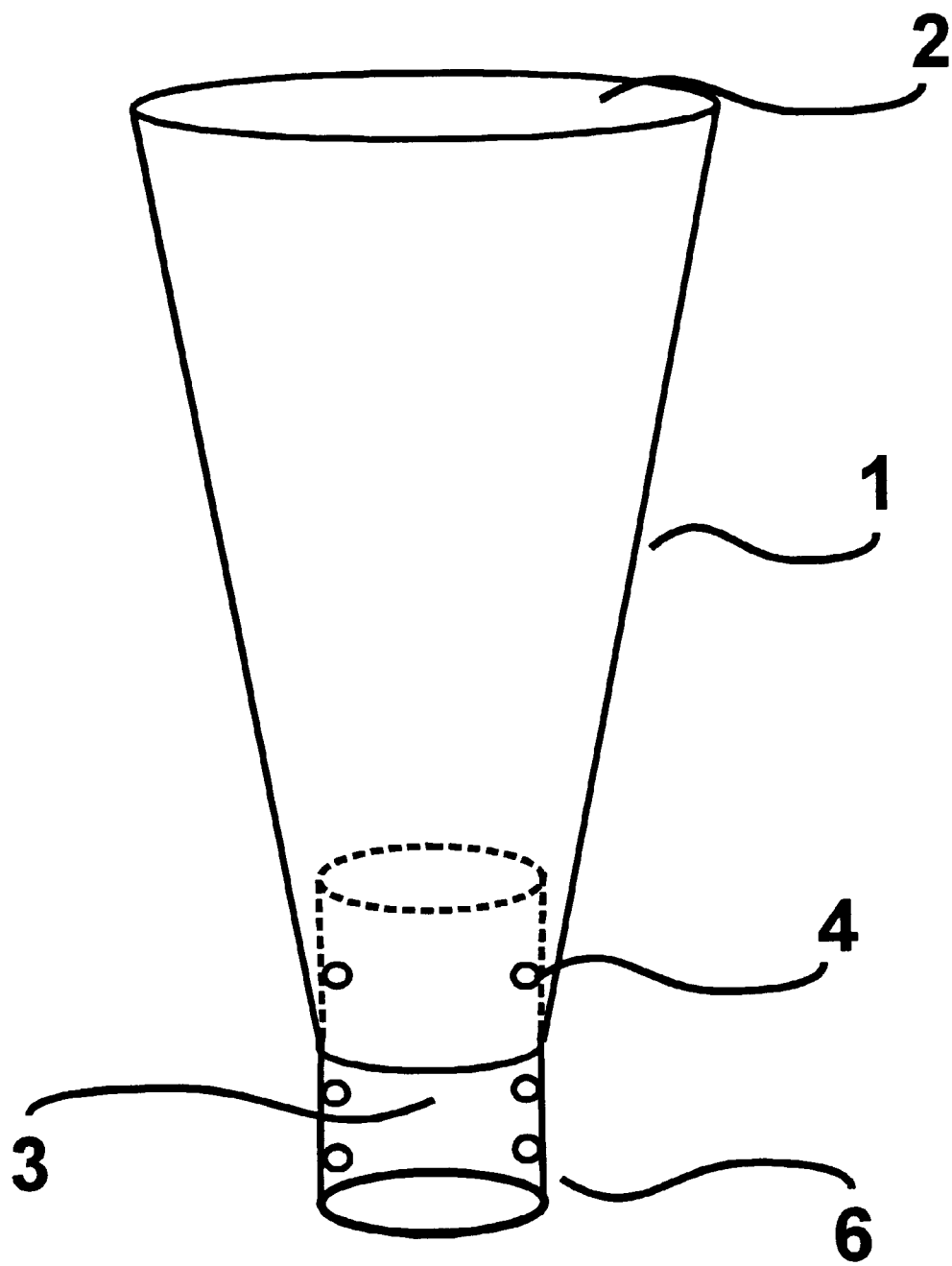
FIG. 3 is an expanded view of one embodiment of a tube, into part of which a column has been inserted wherein particles of a separation medium are directly embedded on the interior surface of said column, according to the present invention.

Furthermore, a second tube or column, hereinafter referred to as a column, can be joined with said tube (1). As shown in FIG. 3, such a column (6) is inserted into the bottom end (3) of the tube (1). As shown in FIG. 3, said column (6) has particles of a separation medium (4) embedded on its interior surface. Similar to the tube (1), each end of said column (6) can be open or closed. Therefore, the ends of said column (6) are selected from the group comprised of an open top end and an open bottom end; an open top end and a closed bottom end; a closed top end and an open bottom end; a closed top end and a closed bottom end; a tapered open end; a tapered closed end; and, combinations thereof.

The tube (1) and column (6) can be joined together in any configuration and by any means including, but not limited to, means selected from the group comprised of heat-based joining;

pressure-based joining; adhesive-based joining; external union based joining and, combinations thereof. Heat based joining includes melting the solid material of which said tube (1) and said column (6) are composed and using any other heat-based methods to join the tube (1) together with the column (6) to form one embodiment of the device described by the present invention.

Adhesive-based joining includes the use of any types of adhesive or bonding materials which react physically or chemically with either the solid material composing the tube (1) or the solid material composing the column (6) or the materials composing both the tube (1) and the column (6).

Figure 4A:
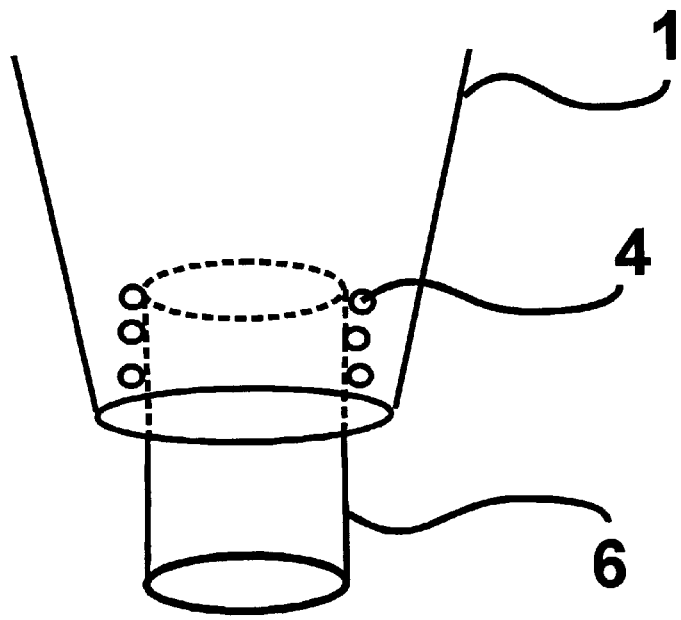
FIG. 4a is an expanded view of one embodiment of a tube, into part of which a column has been inserted wherein particles of a separation medium are directly embedded on the exterior surface of said column, according to the present invention.
Figure 4B:
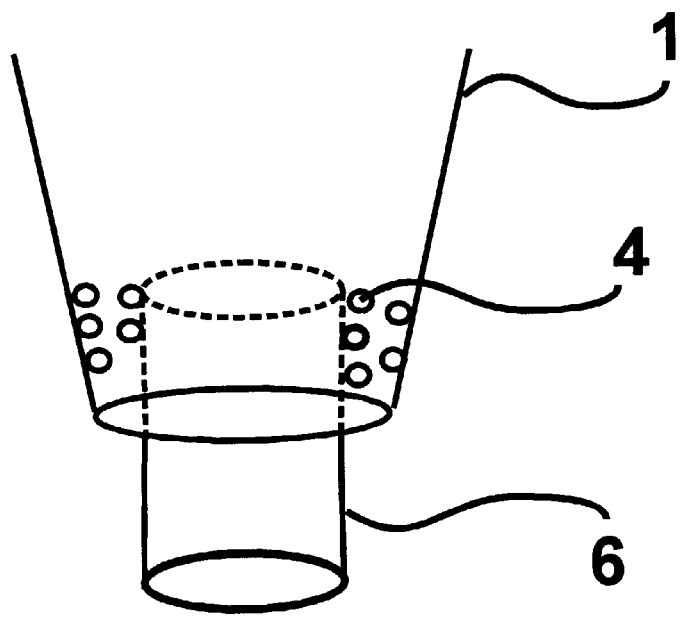
FIG. 4b is an expanded view of one embodiment of a tube, into part of which a column has been inserted wherein particles of a separation medium are directly embedded on the exterior surface of said column and on the interior surface of said tube, according to the present invention.
Figure 5:
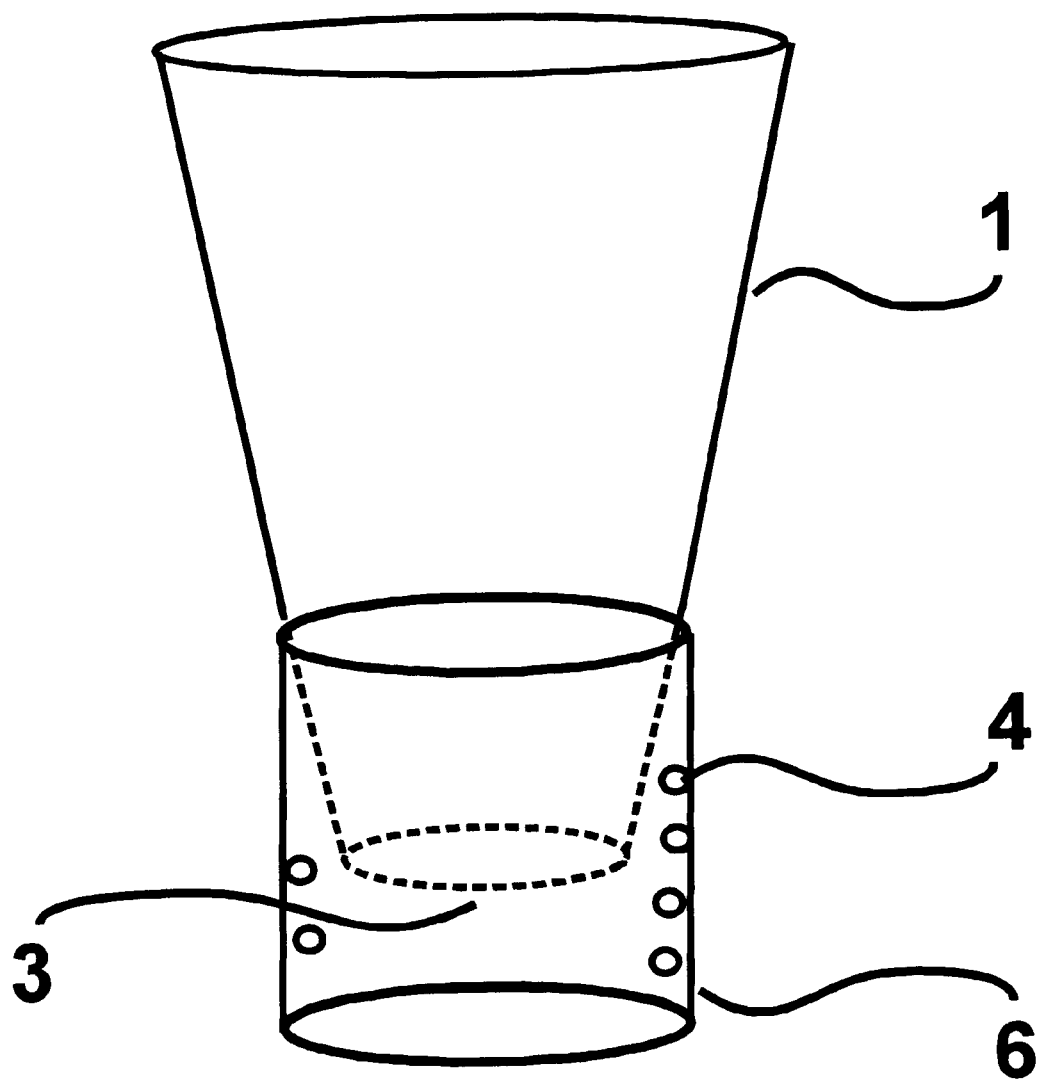
FIG. 5 is an expanded view of one embodiment of a column, into part of which one end of a tube has been inserted wherein particles of a separation medium are directly embedded on the interior surface of said column, according to the present invention.
Figure 6:
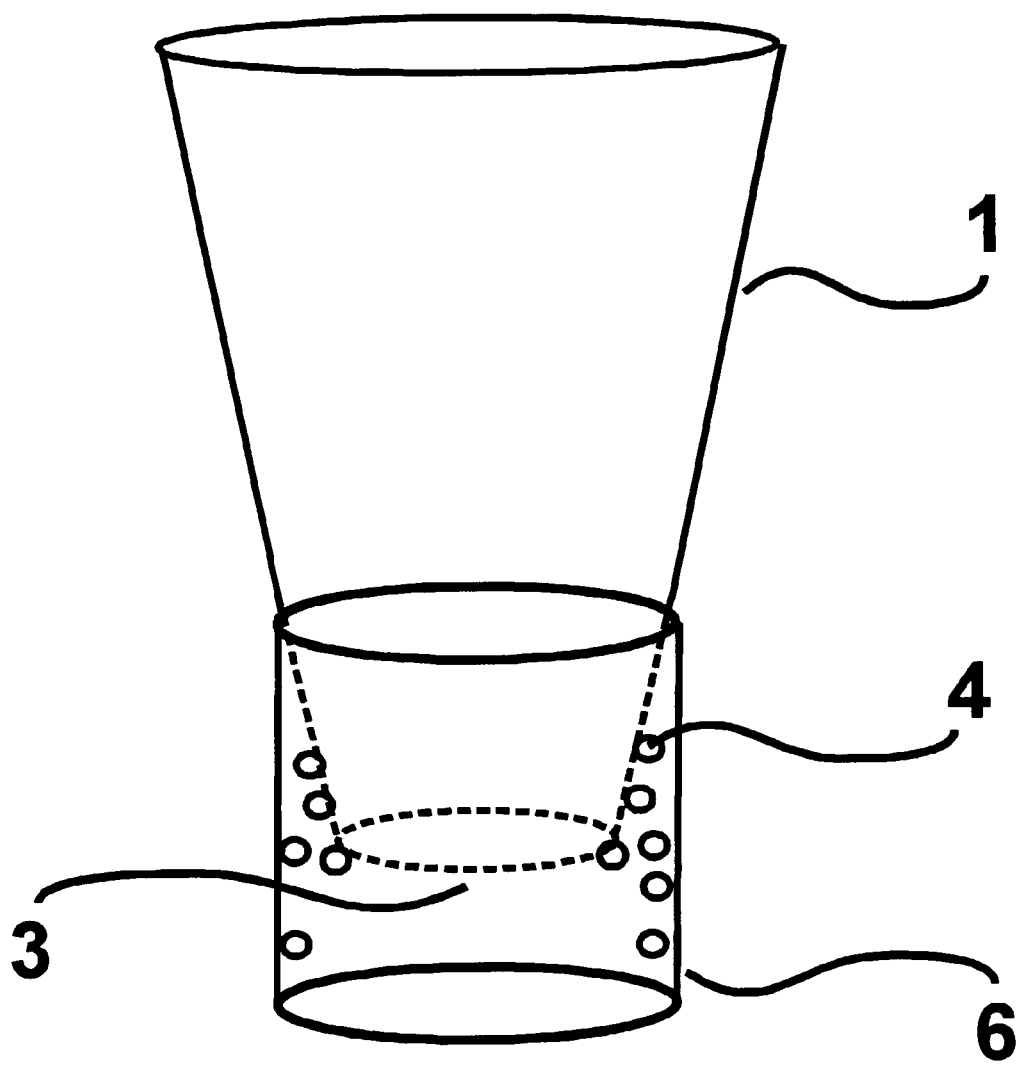
FIG. 6 is an expanded view of one embodiment of a column, into part of which one end of a tube has been inserted wherein particles of a separation medium are directly embedded on the exterior surface of said tube and on the interior surface of said column, according to the present invention.

As shown in FIGS. 4a and 4b, when said column (6) is inserted into said tube (1), the particles of the separation medium (4) can be embedded either on the exterior surface of said column (6), as shown in FIG. 4a or both the exterior surface of said column (6) and the interior surface of said tube (1), as shown in FIG. 4b. Alternatively, the particles of the separation medium (4) could also be embedded just on the interior surface of said tube (1). Furthermore, as shown in FIG. 5, the tube (1) can also be inserted into the column (6). In this figure the bottom end (3) of said tube (1) is inserted into said column (6) where said column has particles of a separation medium (4) embedded on its interior surface. Alternatively, as shown in FIG. 6, particles of the separation medium (4) can be embedded both on the interior surface of said column (6) and the exterior surface of said tube (1).

In FIGS. 3, 4a and 4b said column (6) can be fully or partially inserted within said tube (1) and can be inserted at the top end, the bottom end or by overlapping both ends. In FIGS. 5 and 6 said tube (1) can be partially or fully inserted in said column (6) and can be inserted at the top end, the bottom end or by overlapping both ends. Therefore, the tube (1) and the column (6) can be joined together in a configuration selected from the group comprised of partial insertion of said tube (1) into said column (6); full insertion of said tube (1) into said column (6); partial insertion of said column (6) into said tube (1); full insertion of said column (6) into said tube (1); stacked insertion of two or more columns (6) into said tube (1); stacked insertion of two or more tubes (1) into said column (6); concentric insertion of two or more columns (6) into said tube (1); concentric insertion of two or more tubes (1) into said column; and, combinations (6) thereof.

In addition said tube (1) and said column (6) can be joined in any other configurations suited to the applications of the device described in the present invention. Both said tube (1) and said column (6) can be made of any solid materials suited for the applications described herein. For example, said solid material can consist of a material selected from the group comprised of porous materials, non-porous materials, polyethylene, polypropylene, polytetrafluoroethylene, polysulfone, polyethersulfone, cellulose acetate, polystyrene, polystyrene/acrylonitrile copolymer, PVDF, glass, metal, silica, wood, paper, cardboard, heat shrink materials, and combinations thereof. Heat shrink materials include any materials that change their shape or size upon the application of temperature variations such as the application of heat.

Figure 7:
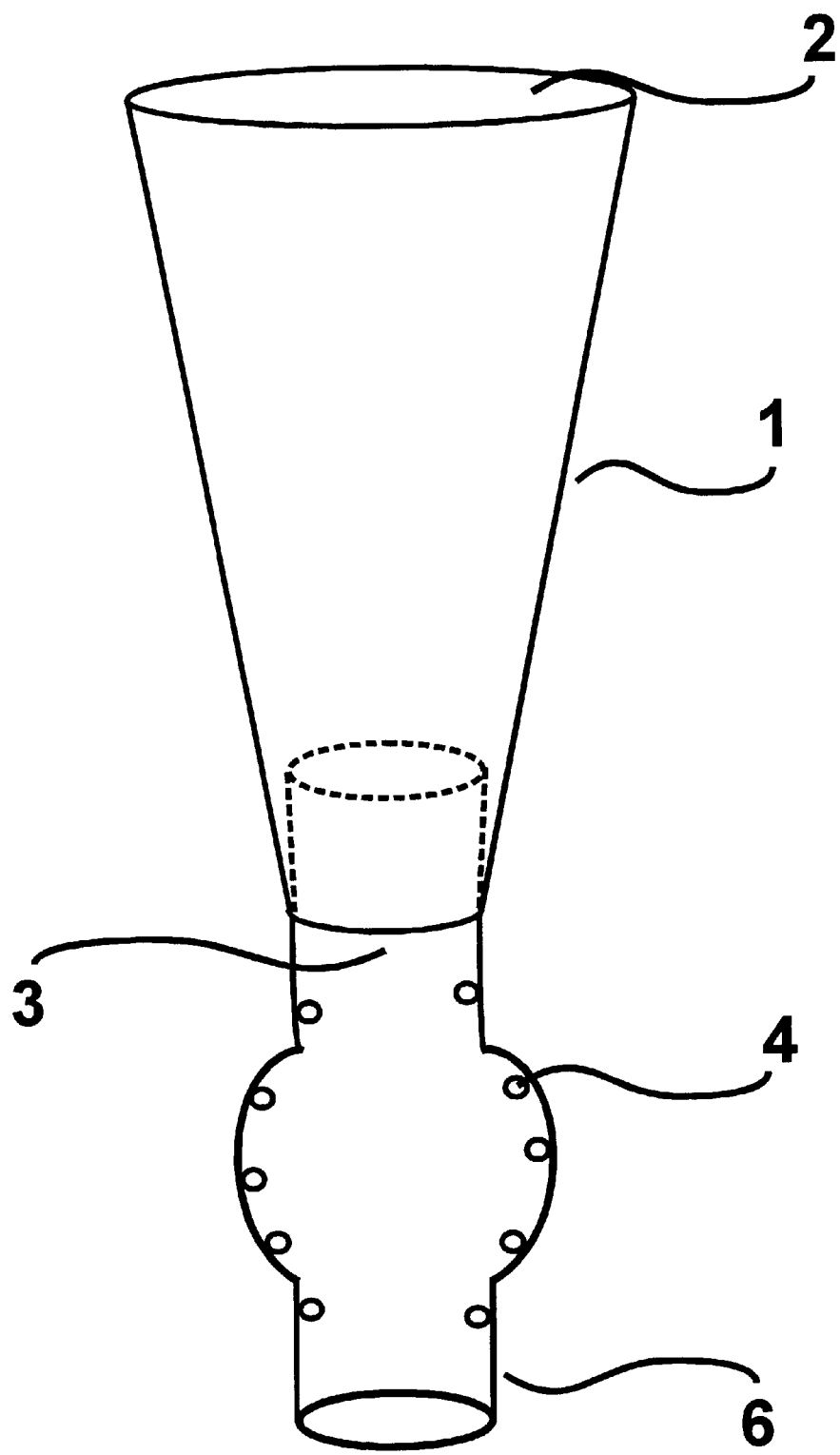
FIG. 7 is an expanded view of one embodiment of a tube, into part of which a column has been inserted wherein particles of a separation medium are directly embedded on the interior surface of said column and wherein said column is of an irregular shape with perpendicular cross sections of varying areas along the length of said column, according to the present invention.

Said tube (1) and said column (6), as described in the figures discussed herein, can be of any shape or configuration and of any length or width, where each dimension of said tube (1) or column (6) can range from one micrometer to hundreds of meters. Furthermore, said tube (1) or column (6) can be a capillary like structure where the diameter of said tube (1) or column (6) can be as small as the size of a separation medium particle and the length of said (1) or column (6) can range from a millimeters to several hundred meters. Also, as shown in FIG. 7, said (1) or column (6) can be of any shape or size such that shape can vary along the length of the (1) or column (6). In FIG. 7, the column (6) has a cylindrical shape, with a spherical shape at its center. In this instance, the cross-sectional area of the column (6) in the spherical region is greater than the cross sectional area in the cylindrical region of said column (6). The cross section of said tube or column is measured as the area of the shape formed when said tube (1) or column is cut by a flat surface perpendicular to length of said tube or column (6).

As described herein, said tube (1) or said column (6) can be of shape selected from, but not limited to, the group comprised of a cylindrical shape; a spherical shape; an elongated shape with a square cross-section; an elongated shape with a rectangular cross-section; an elongated shape with a polygonal cross-section; an elongated shape with an oval cross-section; an elongated shape with an irregularly shaped cross-section; an elongated shape with varying cross-sections along the length of said shape; and, combinations thereof.

Furthermore, said tube (1) or said column (6) can be of any form including of a form selected from the group comprised of a hollow interior form; a partially hollow interior form; and, a solid interior form. Said partially hollow interior form and said solid interior form can consist of said tube (1) or column (6) filled with a separation medium such that particles of said medium (4) are packed said tube (1) or column (6) while still permitting the passage of the sample into or through said tube (1) or column (6).

While the present invention describes any device suited for the applications described herein, said device can also consist of a tube or column wherein said tube or column is selected from the group comprised of a capillary tube; a pipette tip; a chromatography column; and, combinations thereof. Thus, in one embodiment, the present invention could consist of a pipette tip with particles of a separation medium (4) embedded on its surface. Alternatively, in another embodiment, the present invention could consist of a capillary tube with particles of a separation medium (4) embedded on its interior or exterior surface. Furthermore, the tube (1) or column (6) described in the present invention can have additional components that modify said tube or column. For example, said tube (1) or column (6) can have caps, plugs or other mechanisms to close either one of or both its top and bottom ends and where said caps, plugs or mechanisms can be optionally attached to said tube (1) or column (6).

The particles of the separation medium (4) described in the present invention can be any types of particles of any type of separation medium suited for the separation, preparation, analysis, filtration or purification of samples. For example, said separation medium can be a chromatography material selected from the group comprised of, but not limited to, porous chromatography materials; non-porous chromatography materials; silica materials; non-silica materials; polymer-based materials; active charcoal; zirconium; titanium; polystyrene; carbon; affinity chromatography materials; polymers; gels; bacteria; living cells; solid powders; and combinations thereof.

Furthermore, the particles of the separation medium (4) can be chemically, physically or biologically modified. Said particles (4) can be of any shape or size such as a size ranging from micrometers to millimeters in each dimension. In addition, the particles of said separation medium (4) can be of a shape selected from the group comprised of, but not limited to spherical shapes, cubical shapes, cylindrical shapes, oval shapes, irregular shapes, and combinations thereof.

The particles of said separation medium (4) can be directly embedded on the surface of said tube (1) or column (6) by a means selected from the group comprised of, but not limited to, embedding by heat application; embedding by heat based extrusion; embedding by pressure application; embedding by physical force application; embedding by chemical means; embedding by application of electrical current; embedding by ultrasonication; laser based embedding; microwave based embedding; embedding by welding; embedding by blowing; embedding during the manufacture of said tube or column; and, combinations thereof. The separation medium particles can cover any part of the interior or exterior surface of said tube (1) or said column (6).

Figure 8A:
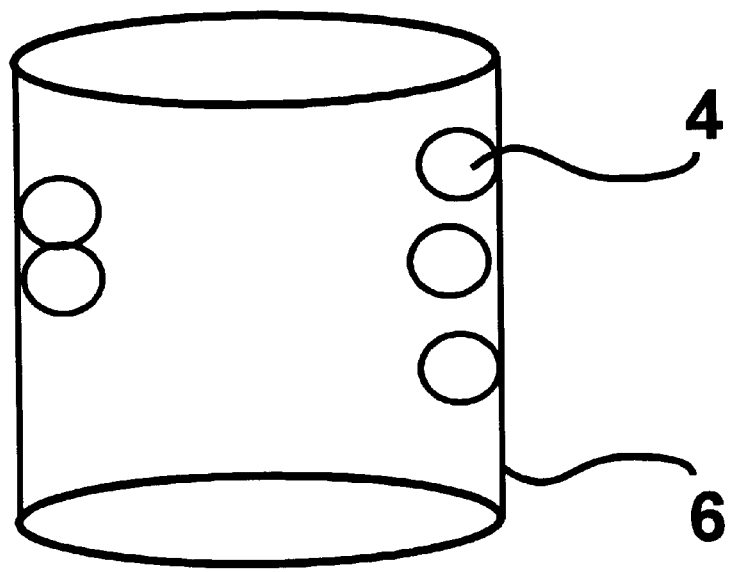
FIG. 8a is an expanded view of one embodiment of a column, wherein particles of a separation medium are directly embedded on the interior surface of said column such that said particles are in contact only with particles immediately adjacent to said particles, according to the present invention.
Figure 8B:
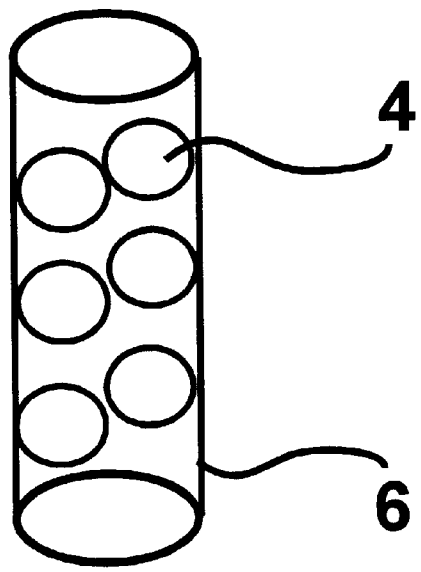
FIG. 8b is an expanded view of one embodiment of a column, wherein particles of a separation medium are directly embedded on the interior surface of said column such that said particles are in contact with particles diagonally across from said particles, according to the present invention.

As shown in figure FIG. 8a, particles of said separation medium (4) can be embedded on the interior surface of said column (6) such that said particles (4) are in contact only with particles (4) immediately adjacent to said particles (4) and such that said particles (4) are not in contact with each other along the central hollow space in the interior of said column (6). FIG. 8b shows particles of a separation medium (4) that are embedded on the interior surface of said column (6) such that said particles (4) are in contact with particles (4) diagonally across from said particles (4) and such that said particles (4) are in contact with other particles along the central hollow space in the interior of said column (6). While FIGS. 8a and 8b are shown for said column (6) in the present invention, said figures could also represent said tube (1), according to the present invention.

Figure 9:
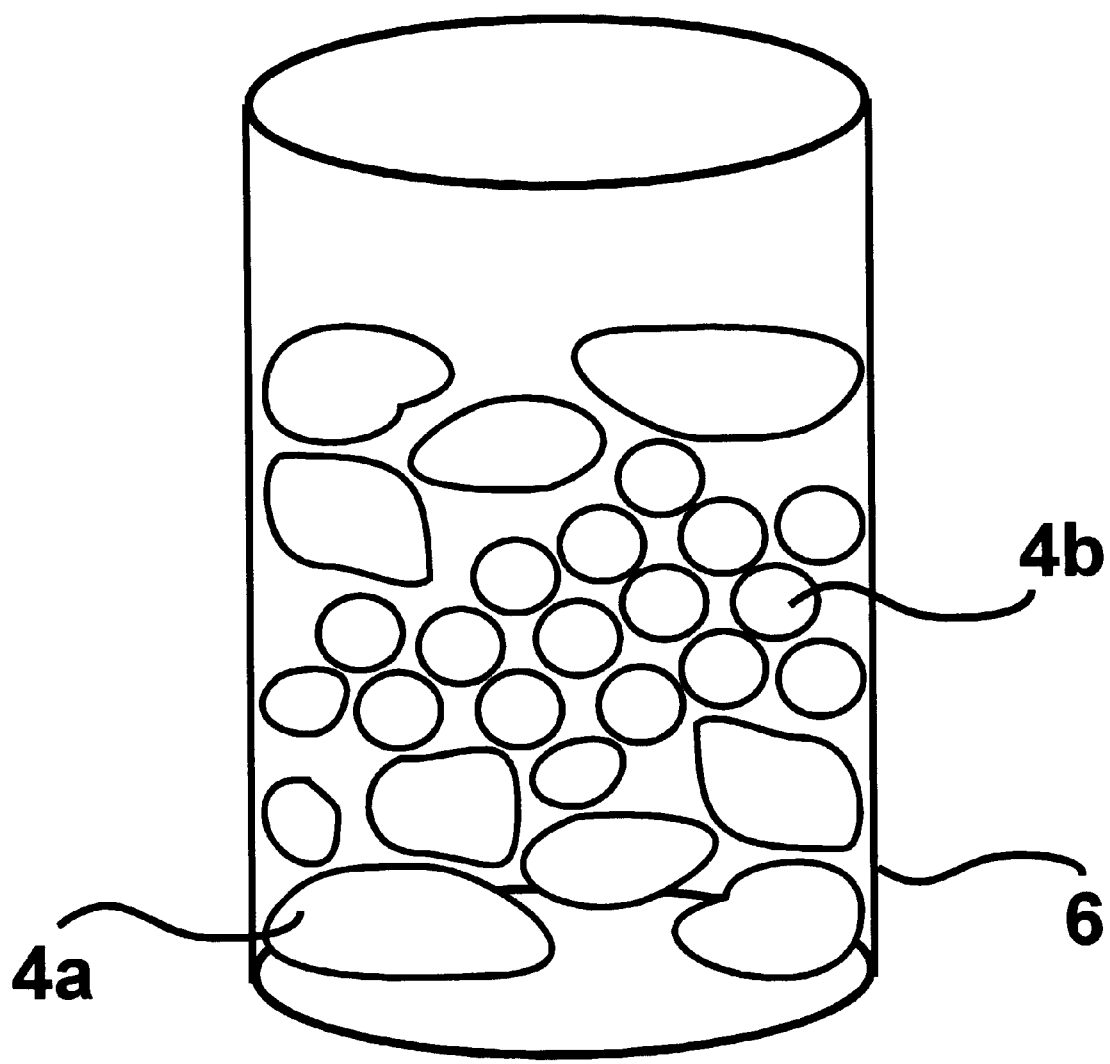
FIG. 9 is an expanded view of one embodiment of a column, wherein different types of particles of a separation medium with different sizes are directly embedded on the interior surface of said column such that said particles are either in contact with the surface of said column or with other particles of the separation medium, according to the present invention.
Figure 10A:
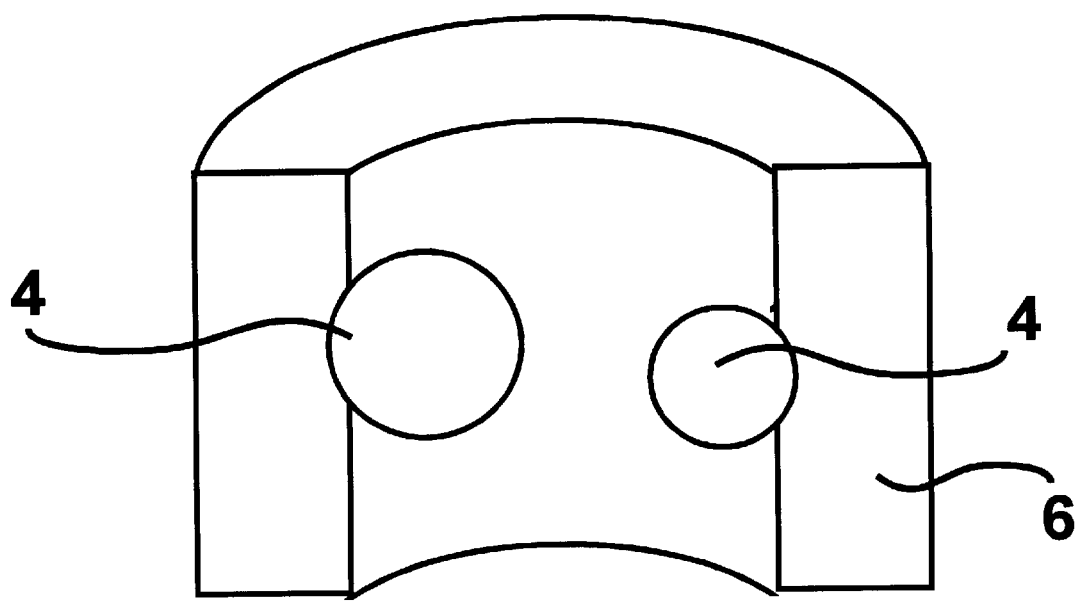
FIG. 10a is an expanded view of one embodiment of a column, wherein particles of a separation medium are directly embedded on the interior surface of said column such that said particles are in contact only with the interior surface of said column.
Figure 10B:
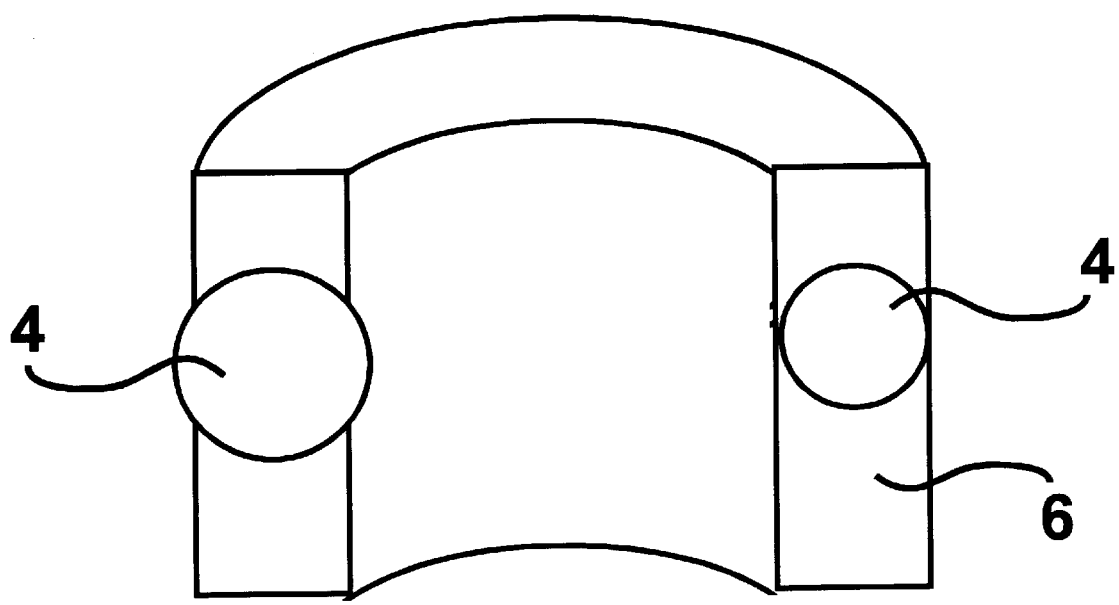
FIG. 10b is an expanded view of one embodiment of a column, wherein particles of a separation medium are fully embedded in the walls of said column such that said particles are optionally in contact with both the interior and exterior surfaces of said column.

FIG. 9 shows different types of particles of a separation medium with different sizes embedded on the interior surface of said column (6) such that said particles are either in contact with the surface of said column (6) or are in contact with other particles of the separation medium. In this figure, selected particles such as the larger irregular particles (4a) are embedded on the interior surface of said column (6) while other particles such as the smaller spherical particles (4b) are contained within said column (6) by said larger particles (4a) without being directly embedded in the surface of said column (6). Said particles (4b) are in contact with other particles (4a or 4b) and are optionally in contact with the surface of said column (6). FIG. 10a shows particles of the separation medium (4) that are partially embedded on the surface of said column (6). FIG. 10b shows particles of said separation medium (4) that are fully embedded within or across the walls of said column (6).

Figure 11:
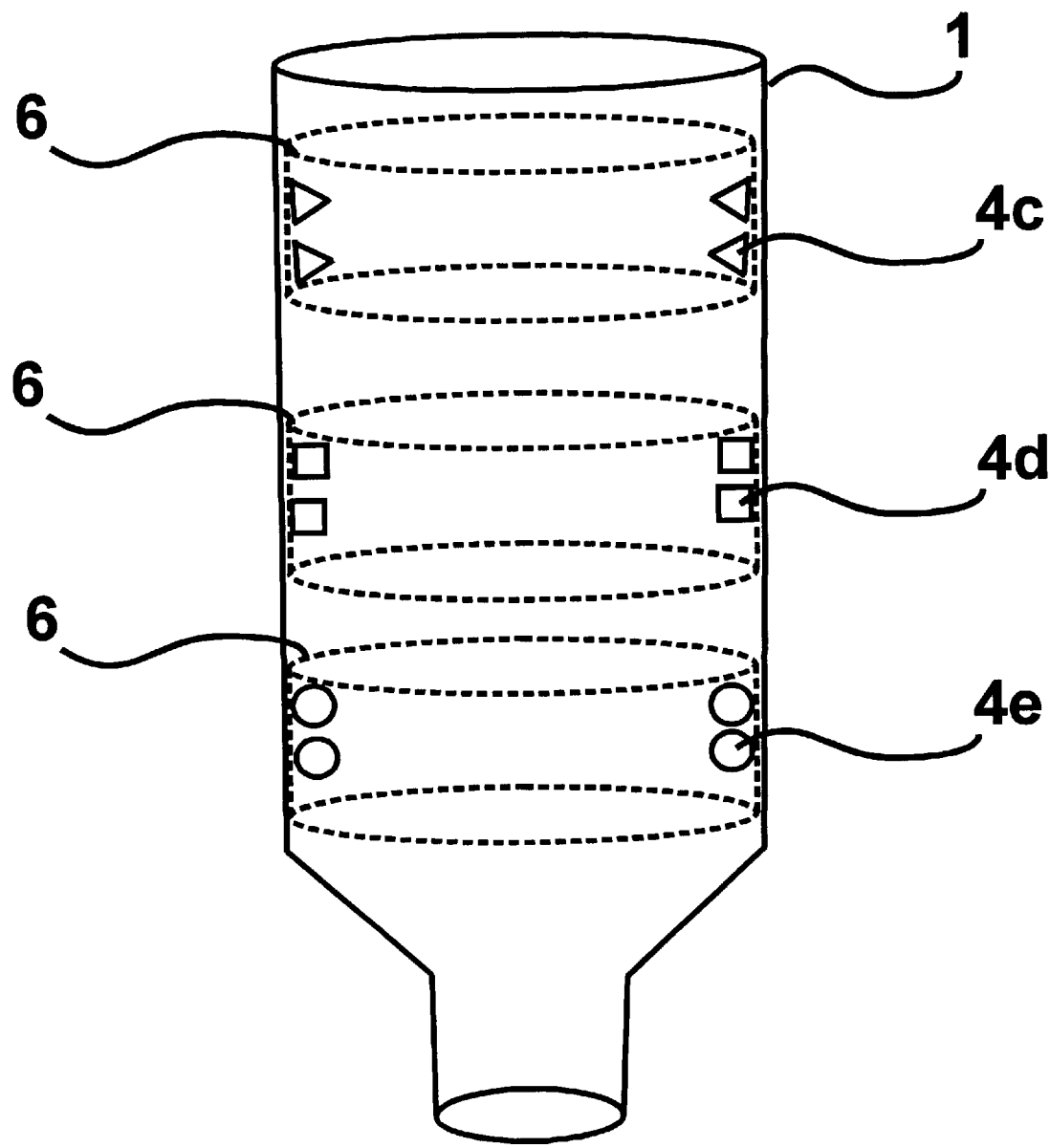
FIG. 11 is an expanded view of one embodiment of a tube, wherein multiple columns with different separation media directly embedded on the surface of each column have been inserted into said tube such that said columns are stacked on top of each other, according to the present invention.

While the prior figures show embodiments of the device, according to the present invention, with one tube and one column, said device could be created in configurations with multiple tubes and columns forming said device. FIG. 11 shows the tube (1) with multiple columns (6) placed in the interior of said tube (1) such that said columns (6) are stacked on top of each other. In the present invention this configuration is referred to as a stacked configuration. Also, as shown in FIG. 11, each of the columns (6) can contain particles of a unique separation medium (4c, 4d or 4e) such that a sample introduced into said tube (1) and columns (6) is separated or purified by each of the different separation media. This configuration allows for performing different separation processes in one step, thus speeding up the sample preparation process. Also, while FIG. 11 shows one configuration for a single tube (1) and multiple columns (6) the device of the present invention could also have a single column (6) and multiple tubes (1).

Figure 12:
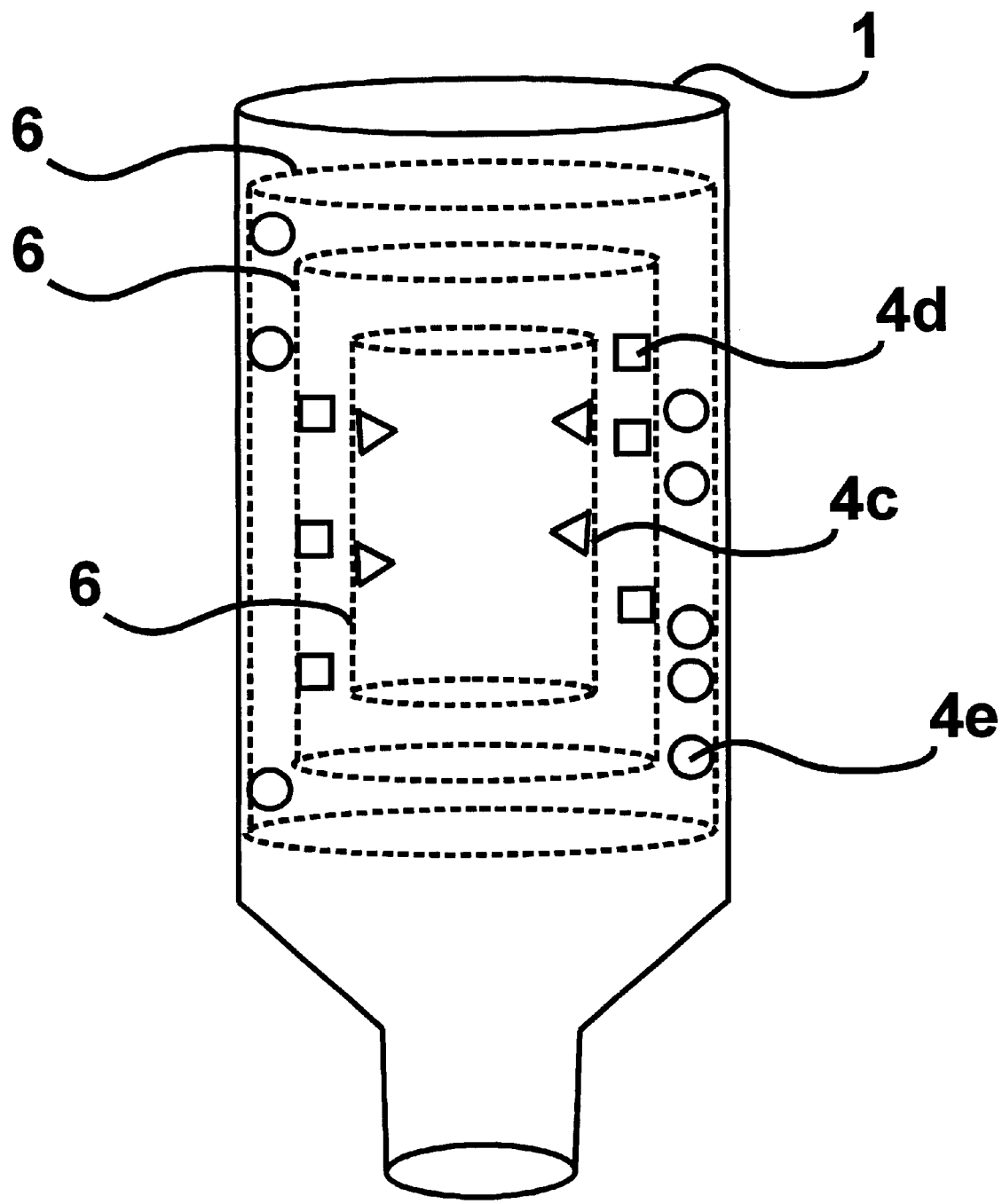
FIG. 12 is an expanded view of one embodiment of a tube, wherein multiple columns are inserted into each other and into said tube such that said columns are partially or fully contained within said tube or within another column and wherein one or more of said columns has particles of a separation medium directly embedded on its interior and/or exterior surface, according to the present invention.

Also, as shown in FIG. 12, multiple columns (6), each with particles of a different separation medium (4c, 4d, or 4e) embedded in it, can be placed inside of each other. In FIG. 12, the column (6) with the separation medium particles labeled 4c is placed inside the column (6) with the separation medium particles labeled 4d, which is placed inside the column (6) with the separation medium particles labeled 4e, which is placed inside said tube (1). In the present invention this configuration is referred to as a concentric configuration because the cross sections of said columns are concentric to each other. This configuration also allows for performing different separation processes in one step, thus speeding up the sample preparation process. Also, while FIG. 12 shows one configuration for a single tube (1) and multiple columns (6) the device of the present invention could also have a single column (6) and multiple tubes (1).

Furthermore, the device described in the present invention can be made by melting the solid material composing said tube (1) or said column (6) in said device such that said tube or said column can be pulled and elongated such that particles of said separation medium (4) are embedded in the solid material composing said tube or column. This method can be used to make capillaries with the separation medium embedded in their interior. The capillaries can be made by heat-based, extrusion-based, pressure-based, air pressure based, vaccum-based, and any other methods.

Figure 13:
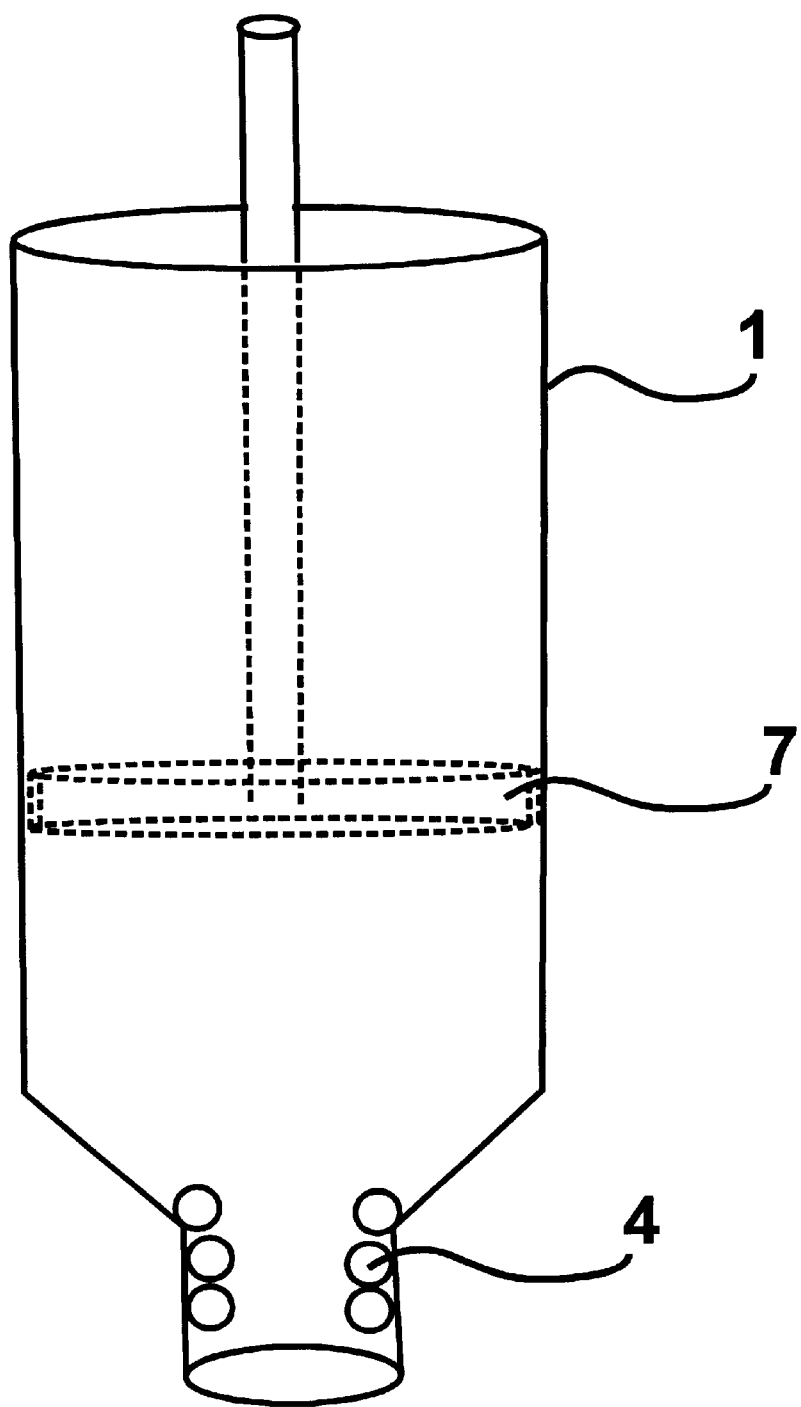
FIG. 13 is an expanded view of one embodiment of a tube, wherein particles of a separation medium are directly embedded on the interior surface of said tube, and wherein a piston is attached to said tube to enhance the flow of samples through said tube, according to the present invention.

In addition to multiple tube and column configurations, the tube or column of the present invention can have a piston or similar tool attached to said tube or column. FIG. 13 shows the tube (1) of the present invention with particles of a separation medium (4) embedded on the interior surface of said tube (1). This figure also shows a piston (7) placed into the interior of said tube (1) such that pressure applied to said piston (7) by lowering it further into the tube (1) can be used to push a sample out of the tube (1). Alternatively, when said piston (7) is raised a sample can be pulled into said tube (1). While FIG. 13 shows a piston, said tube (1) or said column, according to the present invention, can be attached to any such tool where said tool is selected from the group comprised of, but not limited to, a pistol; a syringe; a pipettor; a pressure application tool; a suction tool; and, combinations thereof.

The device, according to the present invention, can be present in any multi-format form such that said device exists as part of a multi-tube or multi-column format selected from the group comprised of 8-, 12-, 24-, 48-, 96-, 384-, 1536- or higher tube or column formats. Furthermore, the present invention can be used for any sample preparation methods wherein said sample preparation methods are selected from the group comprised of chromatography; high pressure liquid chromatography (HPLC); electrophoresis; gel filtration; sample centrifugation; on-line sample preparation; diagnostic kits testing; diagnostic testing; transport of chemicals; transport of biomolecules; high throughput screening; affinity binding assays; purification of said sample; size-based separation of the components of said sample; physical properties based separation of the components of said sample; chemical properties based separation of the components of said sample; biological properties based separation of the components of said sample; electrostatic properties based separation of the components of said sample; and, combinations thereof. Also, the device of the present invention can be part of a larger device or can have a unique function such as being a reaction chamber or spin column.

Furthermore, the present invention can be used for the preparation of any types of sample where said samples are selected from the group comprised of biological samples; protein containing samples; nucleic acid containing samples; lipid containing samples; carbohydrates containing samples; cell containing samples; blood containing samples; tissue containing samples; living matter containing samples; mucus containing samples; serum containing samples; chemical samples; biochemical samples; radioactive samples; and, combinations thereof.

The broader usefulness of the invention may be illustrated by the following examples.

EXAMPLE #1

Use of the Present Invention for Peptide Sample Preparation.

In this experiment, we used a 1–10 micro-liter micro pipette tip and placed a capillary tube 2 mm in length in the bottom end of said pipette tip. The capillary tube was formed by taking a polypropylene tube with a length of 5 cm, an inner diameter of 3 mm and an outer diameter of 5 mm and filling the tube with C-18 separation medium particles, which have dimensions from 40 to 60 microns. The tube was heated and then pulled or extruded such that the separation medium particles were embedded into the interior of said tube due to the melting of the polypropylene material composing said tube. Excess C-18 particles were washed out from the tube. A 2 mm section of the tube containing embedded C-18 particles was cut and placed at the bottom of the pipette tip such that the exterior of the tube was in contact with the interior of the pipette tip.

A 20 micro-liter peptide solution containing buffer was pipetted in and out to the pipette tip by using a micro pipette. The peptide was retained in the tube within the tip while water and impurities passed through the lower opening. The tip was washed with 20 micro-liters of water a few times and the peptide was then eluted from the tube in the tip using 50 percent isopropanol. The purified peptide sample was then analyzed by HPLC.

While a specific embodiment of the invention has been shown and described in detail to illustrate the application of the principles of the invention, it is understood that the invention may be embodied otherwise without departing from such principles and that various modifications, alternate constructions, and equivalents will occur to those skilled in the area given the benefit of this disclosure and the embodiment described herein, as defined by the appended claims.

What is claimed is:

1. A device for the preparation of small sample volumes consisting of a tube of a length from 1 micrometer to 100 meters wherein said tube is made of a solid material enclosing a volume; and, particles of a separation medium are directly embedded on at least part of only the surface of said tube such that said particles adhere to said tube in a random and discontinuous manner, wherein said particles of said separation medium are embedded on the surface of said tube by heat application, by pressure application, or a combination of heat and pressure application.

2. The device of claim 1, wherein the ends of said tube are selected from the group consisting of an open top end and an open bottom end; an open top end and a closed bottom end; a closed top end and an open bottom end; a closed top end and a closed bottom end; a tapered open end; a tapered closed end; and, combinations thereof.

3. The device of claim 1, wherein said tube is of a shape selected from the group consisting of a cylindrical shape; a spherical shape; an elongated shape with a square cross-section; an elongated shape with a rectangular cross-section; an elongated shape with a polygonal cross-section; an elongated shape with an oval cross-section; an elongated shape with an irregularly shaped cross-section; an elongated shape with varying cross-sections along the length of said shape; and, combinations thereof.

4. The device of claim 1, wherein said tube is of a form selected from the group of a hollow interior form; a partially hollow interior form; and, a solid interior form.

5. The device of claim 1, wherein said tube is selected from the group consisting of a capillary tube; a pipette tip; a chromatography column; and, combinations thereof.

6. The device of claim 1, wherein said tube has caps, plugs or other mechanisms to close either one of or both its top and bottom ends and where said caps, plugs or mechanisms are optionally attached to said tube.

7. The device of claim 1, wherein said tube is attached to a tool selected from the group consisting of a pistol; a syringe; a pipettor; a pressure application tool; a suction tool; and, combinations thereof.

8. The device of claim 1, wherein said solid material consists of a material selected from the group consisting of porous materials, non-porous materials, polyethylene, polypropylene, polytetrafluoroethylene, polysulfone, polyetherstlfone, cellulose acetate, polystyrene, polystyrene/acrylonitrile copolymer, PVDF, glass, metal, silica, wood, paper, cardboard, heat shrink materials, and combinations thereof.

9. The device of claim 1, wherein said separation medium is a chromatography material selected from the group consisting of porous chromatography materials; non-porous chromatography materials; silica materials; non-silica materials; polyer-based materials; active charcoal; zirconium; titanium; polystyrene; carbon; affinity chromatography materials; polymers; gels; bacteria; living cells; solid powders; and combinations thereof.

10. The device of claim 1, wherein the particles of said separation medium are chemically, physically or biologically modified.

11. The device of claim 1, wherein the particles of said separation medium are of a size ranging from micrometers to millimeters in each dimension.

12. The device of claim 1, wherein the particles of said separation medium are of a shape selected from the group consisting of spherical shapes, cubical shapes, cylindrical shapes, oval shapes, irregular shapes, and combinations thereof.

13. The device of claim 1, wherein said device exists as part of a multi-tube or multi-column format selected from the group consisting of 8-, 12-, 24-, 48-, 96-, 384-, 1536- or higher tube or column formats.

14. A device for the preparation of small sample volumes consisting of a tube of a length from 1 micrometer to 100 meters wherein said tube is made of a solid material enclosing a volume: and, particles of a separation medium are directly embedded on at least part of only the surface of said tube such that said particles adhere to said tube wherein said device is made by melting the solid material composing said tube such that said tube can be pulled and elongated such that particles of said separation medium are embedded in the solid material composing said tube.

15. The device of claim 1, wherein said tube contains additional particles of a separation medium within it wherein said additional particles are not embedded within said tube.

16. The device of claim 14, wherein said tube contains additional particles of a separation medium within it wherein said additional particles are not embedded within said tube.

* * * * *